United States Patent
Carol et al.

(10) Patent No.: US 6,989,472 B1
(45) Date of Patent: Jan. 24, 2006

(54) CDNA SEQUENCE TRANSCRIBING AN MRNA ENCODING THE TERMINAL OXIDASE ASSOCIATED WITH CAROTENOID BIOSYNTHESIS, AND USES THEREOF

(75) Inventors: Pierre Carol, Grenoble Cedex (FR); Marcel Kuntz, Grenoble Cedex (FR); Regis Mache, Grenoble Cedex (FR)

(73) Assignee: Universite Joseph Fourier, Grenoble Cedex (FR)

( * ) Notice: Subject to any disclaimer, the term of this patent is extended or adjusted under 35 U.S.C. 154(b) by 0 days.

(21) Appl. No.: 09/807,867

(22) PCT Filed: Oct. 20, 1999

(86) PCT No.: PCT/IB99/01719

§ 371 (c)(1),
(2), (4) Date: Jun. 15, 2001

(87) PCT Pub. No.: WO00/23605

PCT Pub. Date: Apr. 27, 2000

(30) Foreign Application Priority Data

Oct. 20, 1998 (FR) ............................................ 98 13283

(51) Int. Cl.
*C12N 15/29* (2006.01)
*C12N 15/52* (2006.01)
*C12N 15/82* (2006.01)

(52) U.S. Cl. ...................... 800/282; 800/278; 800/298; 435/468

(58) Field of Classification Search ................. 800/278, 800/282, 298; 536/23.1, 23.2, 23.6; 435/419, 435/468

See application file for complete search history.

(56) References Cited

U.S. PATENT DOCUMENTS 5,618,988 A * 4/1997 Hauptmann .................. 800/205

FOREIGN PATENT DOCUMENTS

| WO | WO 91/09128 | 6/1991 |
| WO | WO 92/08798 | 5/1992 |
| WO | WO 95/34668 | 12/1995 |

OTHER PUBLICATIONS

Josse et al, A Plastid Terminal Oxidase Associated with Carotenoid Desaturation during Chromoplast Differentiation, 2000. Plant Phlysiology vol. 123 pp. 1427–1436.*
Josse et al. A Plastid Terminal Oxidase Associated with Carotenoid Desaturation during Chromoplast Differentiation, 2000. Plant Phlysiology, vol. 123, pp. 1427–1436.*
Carol P. et al. GenBank Accession No. AJ004881, submitted Mar. 8, 1998).*
Wu D., et al. GenBank Accession No. AF098072, submitted Oct. 9, 1998.*
Broun P. et al. Science vol. 282; Nov. 13, 1998, pp. 1315–1317.*
Carol P., et al. Trends in Plant Science; Jan. 2001; vol. 6, No. 1; pp. 31–36.*
Fray R. et al. The Plant Journal 1995; vol. 8, No. 5; pp. 693–701.*
Wetzel, Carolyn M., et al., "Nuclear–organelle interactions: the immutans variegation mutant of *Arabidopsis* is plastid autonomous and impaired in carotenoid biosynthesis," The Plant Journal, vol. 6, No. 2, pp. 161–175, 1994.
Newman, T., et al., "Genes galore: a summary of methods for accessing results from large–scale partial sequencing of anonymous *Arabidopsis* cDNA clones," Plant Physiol., vol. 106, pp. 1241–1255 (1994) (Abstract).
Bevan, M., et al., Abstract, XP–002110648, Accession No. AL021712, 1998.
Bevan, M., et al., Abstract, XP–002110649, Accession, No. 049631, 1998.
Finnegan, P.M., et al., Abstract, XP–002110650, Accession No. O03376, 1998.
Finnegan, Patrick M., et al., "Differential Expression of the Multigene Family Encoding the Soybean Mitochondrial Alternative Oxidase," Plant Physiol., vol. 114, No. 2, pp. 455–466, 1997.
Carol, Pierre, et al., "Mutations in the *Arabidopsis* Gene IMMUTANS Cause a Variegated Phenotype by Inactivating a Chloroplast Terminal Oxidase Associated with Phytoene Desaturation," The Plant Cell, vol. 11, pp. 57–68, 1999.
Wu, Dongying, et al., "The *IMMUTANS* Variegation Locus of *Arabidopsis* Defines a Mitochondrial Alternative Oxidase Homolog That Functions during Early Chloroplast Biogenesis," The Plant Cell, vol. 11, pp. 43–55, 1999.
Smith, H., "Photosynthetic Pigmentation–Variegations on a Theme," The Plant Cell, vol. 11, pp. 1–3, 1999.
Sambrook et al., Molecular Cloning, A Laboratory Manual, Second Edition, pp. 8.46–8.52, 9.31 and 9.47–9.55, 1989.
Deikman, Jill, et al., "Separation of cis elements responsive to ethylene, fruit development, and ripening in the 5'–flanking region of the ripening–related E8 gene," Plant Molecular Biology, vol. 37, pp. 1001–1011, 1998.
Pear, Julie R., et al., "Isolation and characterization of a fruit–specific cDNA and the corresponding genomic clone from tomato," Plant Molecular Biology, vol. 13, pp. 639–651, 1989.

(Continued)

Primary Examiner—David T. Fox
Assistant Examiner—Russell Kallis
(74) Attorney, Agent, or Firm—Oliff & Berridge, PLC

(57) ABSTRACT

The invention concerns a cDNA (complementary deoxyribonucleic acid) sequence represented by SEQ ID NO: 1, transcribing a mRNA (messenger deoxyribonucleic acid), itself coding for the TOCB (terminal oxydase associated with carotenoid biosynthesis) represented by SEQ ID NO: 2, and the complementary sequence of SEQ ID NO: 1, vectors transforming cell, plant or fragment of plant, and the method for modifying the production of carotenoids in a plant.

6 Claims, 5 Drawing Sheets

OTHER PUBLICATIONS

Long, D., et al., "The maize transposable element system Ac/Ds as a mutagen in *Arabidopsis*: Identification of an albino mutation induced by Ds insertion," Proc. Natl. Acad. Sci. USA, vol. 90, pp. 10370–10374, 1993.

Whitelam, Garry C., et al., "Phytochrome A Null Mutants of *Arabidopsis* Display a Wild–Type Phenotype in White Light," The Plant Cell, vol. 5, pp. 757–768, 1993.

Altschul, Stephen F., et al., "Gapped BLAST and PSI–BLAST: a new generation of protein database search programs," Nucleic Acids Research, vol. 25, No. 17, pp. 3389–3402, 1997.

Altschul, Stephen F., et al., "Basic Local Alignment Search Tool," J. Mol. Biol., vol. 215, pp. 403–410, 1990.

* cited by examiner

FIG. 1

```
1
CCG CTC ACA TTG GGA TTC GTC ATT CTT CTT CTA AAA CCC GCA AAA TTT CTC CAT TTC TAC
61
CAA AAA TAT CCA ACT TTT ACT TTT CTT TCC TGT GAA ATT ATC TGC TCA AAT CTT TGG TTC
121
CTG ACG GAG ATG GCG GCG ATT TCA GGC ATC TCC TCT GGT ACG TTG ACG ATT TCA CGG CCT
            M   A   A   I   S   G   I   S   S   G   T   L   T   I   S   R   P
181
TTG GTT ACT CTT CGA CGC TCT AGA GCC GCC GTT TCG TAC AGC TCC TCT CAC CGA TTG CTT
L   V   T   L   R   R   S   R   A   A   V   S   Y   S   S   S   H   R   L   L
241
CAT CAT CTT CCT CTC TCT TCT CGT CGT CTG CTA TTA AGG AAC AAT CAT CGA GTC CAA GCA
H   H   L   P   L   S   S   R   R   L   L   L   R   N   N   H   R   V   Q * A
301
ACG ATT TTG CAA GAC GAT GAA GAG AAA GTG GTG GTG GAG GAA TCG TTT AAA GCC GAG ACT
T   I   L   Q   D   D   E   E   K   V   V   V   E   E   S   F   K   A   E   T
361
TCT ACT GGT ACA GAA CCA CTT GAG GAG CCA AAT ATG AGT TCT TCT TCA ACT AGT GCT TTT
S   T   G   T   E   P   L   E   E   P   N   M   S   S   S   T   S   A   F
421
GAG ACA TGG ATC ATC AAG CTT GAG CAA GGA GTG AAT GTT TTC CTT ACA GAC TCG GTT ATT
E   T   W   I   I   K   L   E   Q   G   V   N   V   F   L   T   D   S   V   I
481
AAG ATA CTT GAC ACT TTG TAT CGT GAC CGA AGA TAT GCA AGG TTC TTT GTT CTT GAG ACA
K   I   L   D   T   L   Y   R   D   R   T   Y   A   R   F   F   V   L   E   T
541
ATT GCT AGA GTG CCT TAT TTT GCG TTT ATG TCT GTG CTA CAT ATG TAT GAG ACC TTT GGT
I   A   R   V   P   Y   F   A   F   M   S   V   L   H   M   Y   E   T   F   G
601
TGG TGG AGG AGA GCA GAT TAT TTG AAA GTA CAC TTT GCT GAG AGC TGG AAT GAA ATG CAT
W   W   R   R   A   D   Y   L   K   V   H   F   A   E   S   W   N   E   M   H
661
CAC TTG CTC ATA ATG GAA GAA TTG GGT GGA AAT TCT TGG TGG TTT GAT CGT TTT CTG GCT
H   L   L   I   M   E   E   L   G   G   N   S   W   W   F   D   R   F   L   A
721
CAG CAC ATA GCA ACC TTC TAC TAC TTC ATG ACA GTG TTC TTG TAT ATC TTA AGC CCT AGA
Q   H   I   A   T   F   Y   Y   F   M   T   V   F   L   Y   I   L   S   P   R
781
ATG GCA TAT CAC TTT TCG GAA TGT GTG GAG AGT CAT GCA TAT GAG ACT TAT GAT AAA TTT
M   A   Y   H   F   S   E   C   V   E   S   H   A   Y   E   T   Y   D   K   F
841
CTC AAG GCC AGT GGA GAG GAG TTG AAG AAT ATG CCT GCA CCG GAT ATC GCA GTA AAA TAC
L   K   A   S   G   E   E   L   K   N   M   P   A   P   D   I   A   V   K   Y
901
TAT ACG GGA GGT GAC TTG TAC TTA TTT GAT GAG TTC CAA ACA TCA AGA ACT CCC AAT ACT
Y   T   G   G   D   L   Y   L   F   D   E   F   Q   T   S   R   T   P   N   T
961
CGA AGA CCA GTA ATA GAA AAT CTA TAC GAT GTG TTT GTG AAC ATA AGA GAT GAT GAA GCA
R   R   P   V   I   E   N   L   Y   D   V   F   V   N   I   R   D   D   E   A
1021
GAA CAC TGC AAG ACA ATG AGA GCT TGT CAG ACT CTA GGC AGT CTG CGT TCT CCA CAC TCC
E   H   C   K   T   M   R   A   C   Q   T   L   G   S   L   R   S   P   H   S
1081
ATT TTA GAT GAT GAT GAT ACT GAA GAA GAA TCA GGG TGT GTT GTT CCT GAG GAG GCT CAT
I   L   D   D   D   D   T   E   E   E   S   G   C   V   V   P   E   E   A   H
1141
TGC GAA GGT ATT GTA GAC TGC CTC AAG AAA TCC ATT ACA AGT TAA TAA ATT AGA AAG TAA
C   E   G   I   V   D   C   L   K   K   S   I   T   S
1201
ACT AAA AAA GAT TAT TTG TAT CAG CTC ATG AAC AAT AGA TAT AAT CCC ATA TAC TTG GGA
1261
ATA AAG GAA TAA TGT GAA ATT CCC ATC GTT GTG CTA GTG TGT GAG AGA ATC AAA TAC CCT
1321
AAT GAT GTA AAT GTA CTT TGA TGA GCT TAA GTC GTT GTA GAC CAT TTT ATC AAA AAA AAA
1381
AAA AAA AAA AAA AAA A
```

FIG. 2

```
IMM : 111  FLTDSVIKILDTLYRDRTYA-REEVIETIARVPVAFAFMSVEHMYETFGWWRRADYLKVHF 169
            + T  +++I    L+  R Y  R   +LET+A VP        +LH+              ++K
AOX : 136  YRTVKLLRIPTDLFFKRRYGCRAMMIETNAAVPCMWGGMLEHLRSLRKFQQSGGWIKALL 195

IMM : 170  AESWNEMHHLLIMEELGGNSWFDREETAQHPALRVAMTNYTHESPRMAYHFSECVESH   229
            E+ NE  HL+ M EL      W++R L       +           LYILSP++A+      +E
AOX : 196  EEAENERMHLMTMVEL-VKPKWYERHLWLRVOGVERNAEMVXZESPKVAHRIVGYLEEE 254

IMM : 230  AYETYDKFLK-ASGEELKNMPAPDIAVKYYTGGDLYLFDEFQTSRTPNTRRPVIENLYDV 288
            A   +Y ++LK             ++N+PAP IA+ Y+                  R P    L DV
AOX : 255  AIHSYTEYLKDLESGAIENVPAPAIAIDW---------------------RLPKDARLKDV 295

IMM : 289  FVNIRDDEAEH 299
            IR DEA H
AOX : 296  ITVIRADEAHH 306
```

FIG. 3A

```
T     1  MAISISAMSFGTSVSSYSCFRARSPEKSSVLCNSQNPCRFNSVFP.IRKSDGASRCSVSR
P     1  MAISISAMSFRTSVSS.......SY..SAFLCNSKNPFCLNSLFS.LRNSHRTFQPSLSR
A     1  MA.AISGISSGTLTIS........RPLVTLRRSRAAVSYSSSHRLLHHLPLSSRRLLLR
consensus
      1  MA  ISamS  T    S              L  S       S     lr       1 R T    60  KSCRVRATLLQENEEEVVVEKSFAPKSFPDNVGGGSNGKPPDDSSS.NGLEKWVIKLEQS
P    51  KSSRVRATLLKENEEEVVVEKSFAPKSFPGNVGGGNNGEPPDNSSS.NGLEKWVIKIEQS
A    51  NNHRVQATILQDDEEKVVVEESFKAE...TSTGTEPLEEPNMSSSSTSAFETWIIKLEQG
consensus
     61     RV ATlL e EE VVVE SF       G      P   SSS  g E WvIKlEQ T   119  VNILLTDSVIKILDTLYHNRNYARFFVLETIARVPYFAFISVLHMYESFGWWRRADYMKV
P   110  VNIFLTDSVIKILDTLYHDRHYARFFVLETIARVPYFAFISVLHLYESFGWWRRADYLKV
A   108  VNVFLTDSVIKILDTLYRDRTYARFFVLETIARVPYFAFMSVLHMYETFGWWRRADYLKV
consensus
    121  VNi LTDSVIKILDTLYh R YARFFVLETIARVPYFAFiSVLHlYEsFGWWRRADYlKV T   179  HFAESWNEMHHLLIMEELGGNAWWFDRFLAQHIAIFYYFMTVLMYALSPRMAYHFSECVE
P   170  HFAESWNEMHHLLIMEELGGNAWWFDRFLAQHIAVFYYFMTVSMYALSPRMAYHFSECVE
A   168  HFAESWNEMHHLLIMEELGGNSWWFDRFLAQHIATFYYFMTVFLYILSPRMAYHFSECVE
Consensus
    181  HFAESWNEMHHLLIMEELGGN WWFDRFLAQHIA PYYFMTV mY LSPRMAYHFSECVE T   239  SHAYETYDKFIKDQGEELKNLPAPKIAVDYYTGGDLYLFDEFQTSREPNTRRPKIDNLYD
P   230  HHAYETYDKFIKDQEAELKKLPAPKIAVSYYTGGDLYLFDEFQTSREPNTRRPKIDNLYD
A   228  SHAYETYDKFLKASGEELKNMPAPDIAVKYYTGGDLYLFDEFQTSRTPNTRRPVIENLYD
Consensus
    241   HAYETYDKFlK   ELK lPAP IAV YYTGGDLYLFDEFQTSR PNTRRP IdNLYD T   299  VFMNIRDDEAEHCKTMKACQTHGSLRSPHTD.PCDDSEDDTGCSVP.QADCIGIVDCIKK
P   290  VFMNIRDDEAEHCKTMKACQTHGSLRSPHTN.PCDESEDDPGCSVP.QADCVGIVDCITK
A   288  VFVNIRDDEAEHCKTMRACQTLGSLRSPHSILDDDDTEEESGCVVPEEAHCEGIVDCLKK
Consensus
    301  VFmNIRDDEAEHCKTMkACQT GSLRSPHt    DdsEdd GC VP  A C GIVDCl K
```

FIG. 3B

```
T    357  SVTDTQVTKR
P    348  SVADPNVGRR
A    348  SITS......
Consensus
     361  Sv
```

CDNA SEQUENCE TRANSCRIBING AN MRNA ENCODING THE TERMINAL OXIDASE ASSOCIATED WITH CAROTENOID BIOSYNTHESIS, AND USES THEREOF

The invention relates to a DNA (deoxyribonucleic acid) sequence described by SEQ ID NO:1, transcribing an mRNA (messenger deoxyribonucleic acid), itself encoding the TOCB (Terminal Oxidase associated with Carotenoid Biosynthesis) enzyme described by SEQ ID NO:2, and to vectors for transforming a cell, plant or fragment of a plant, and a process for modifying the production of carotenoids in a plant.

Carotenoids are lipophilic pigments synthesized in plants, fungi and bacteria. In photosynthetic tissues, carotenoids serve as an additional light-absorbing pigment and especially provide photoprotection against free radicals, such as singlet oxygen.

In plants and certain microorganisms, the carotenoid biosynthesis route produces carotenes, xanthophylls and derivatives thereof. These compounds are synthesized from phytoene which is modified by successive dehydrogenation reactions to give phytofluene, zeta-carotene, neurosporene and then lycopene. Lycopene accumulates in certain cases, for example giving the red pigment of tomatoes, or is more generally found in a form modified by cyclization, to form alpha- or beta-carotene. These cyclized carotenoids are the precursors of vitamin A, and may accumulate or give xanthophylls by oxidation reactions, these xanthophylls being yellow, pink, orange or red pigments.

The successive steps of dehydrogenation of phytoene are catalyzed in most microorganisms by a single enzyme known as phytoene desaturase CRTI. In plants and cyanobacteria, two related enzymes exist. The first, known as phytoene desaturase (PDS), catalyzes the conversion of phytoene to phytofluene and then into zeta-carotene. The second, known as zeta-carotene desaturase (ZDS), catalyzes the conversion of zeta-carotene into neurosporene and then into lycopene. Each of these dehydrogenation reactions requires the transfer of two electrons and two protons from the substrate to an acceptor. These dehydrogenation reactions thus require enzymes, known as structural enzymes, and co-factors, which are intermediates in the redox reactions.

The inventors of the present invention have discovered a new gene encoding an enzyme known as TOCB (Terminal Oxidase associated with Carotenoid Biosynthesis), which is involved in carotenoid biosynthesis. It appears that this enzyme is placed in the membranes of chloroplasts and is essential for the correct functioning of PDS.

A first subject according to the invention thus relates to a DNA sequence comprising at least one coding region consisting of:
 the nucleotide sequence represented by SEQ ID NO:1 transcribing an mRNA, this mRNA encoding the TOCB (Terminal Oxidase associated with Carotenoid Biosynthesis) enzyme described by SEQ ID NO:2,
 the modified nucleotide sequence of the sequence SEQ ID NO:1, as described above, particularly by mutation and/or addition and/or deletion and/or substitution of one or more nucleotide(s), this modified sequence transcribing an mRNA which itself encodes the TOCB described by SEQ ID NO:2, or encoding a modified protein of said TOCB, said modified protein having enzymatic activity which is equivalent to that of the TOCB represented by SEQ ID NO:2.

In particular, the invention relates to the coding sequences of tomato TOCB, identified by SEQ ID NO:5, and of capsicum TOCB, identified by SEQ ID NO:3, respectively, and any derived sequence obtained by modifying these sequences.

The gene encoding TOCB is a duplex DNA, comprising introns and exons. The sequence SEQ ID NO:1 is the complementary strand (without the introns) or cDNA, corresponding to the DNA strand transcribing the mRNA encoding TOCB.

The expression "equivalent enzymatic activity" means that, although some of the portions of the enzyme may be structurally modified, it is nevertheless capable of modifying its substrate. Its activity is substantially the same as that of the native enzyme. It will be understood that this enzyme cannot be modified at its active site. Consequently, any modification made to the native sequence, by addition, deletion or substitution of one or more amino acids, is understood as giving rise to an equivalent enzymatic activity insofar as the activity of the native protein is not affected by these modifications.

A second subject according to the invention relates to a DNA sequence comprising at least one coding region consisting of:
 the complementary nucleotide sequence represented by SEQ ID NO:1, this sequence transcribing an antisense mRNA capable of pairing with the mRNA transcribed by the complementary sequence of SEQ ID NO:1,
 the modified nucleotide sequence of the sequence described above, by mutation and/or addition and/or deletion and/or substitution of one or more nucleotide (s), this modified sequence transcribing an antisense mRNA capable of pairing with an mRNA mentioned above,
 a fragment of one of the nucleotide sequences mentioned above, said fragment transcribing an antisense mRNA capable of pairing with the mRNA encoded by the complementary sequence of SEQ ID NO:1.

The term "DNA" may be understood as meaning complementary DNA (or cDNA), i.e. the copy of the mRNA in its DNA form by virtue of the action of a reverse transcriptase. The cDNA does not comprise the introns of the DNA sequences.

In the present invention, the expression "capable of pairing" means the fact that, under given hybridization conditions, the complementary nucleotide sequences pair up. A person skilled in the art clearly knows, depending on the hybridization conditions used, what percentage of identity the sequences must have in order for a pairing or a hybridization to be able to take place. The stringency conditions for obtaining a pairing of similar sequences are, for example, a hybridization in 50% formamide at 35° C. As regards the hybridization conditions, reference will be made in particular to the article "Molecular Cloning, a laboratory manual, second edition, Sambrook, Fritch & Maniatis, 1989, Cold Spring Harbor Laboratory Press, Cold Spring Harbor, N.Y., USA".

In the present invention, the expression "modified nucleotide sequence" means any nucleotide sequence which has a degree of identity with the reference sequence of less than 100%.

According to one preferred embodiment according to the invention, the modified nucleotide sequences according to the present invention comprise approximately at least 70% and better still at least 80% of nucleotides that are identical to those of the nucleotide sequence represented by SEQ ID NO:1, or of its complementary sequence.

The expression "nucleotide identity" means the comparison, when the two strands are aligned, of the sequence of identical nucleotides present on the two strands. Consequently, by reducing to the total number of nucleotides, the percentage of identical nucleotides, i.e. the nucleotide identity, is obtained.

A third subject according to the invention relates to an mRNA transcribed from the DNA sequence according to the definition of the first subject, and more particularly transcribed from the DNA sequence represented by SEQ ID NO:1, said mRNA encoding the TOCB enzyme described by SEQ ID NO:2, or a fragment or a modified protein of the enzyme, and having activity which is equivalent to that of said enzyme in the plant.

A fourth subject according to the invention relates to an antisense mRNA transcribed from the DNA sequence according to the second subject of the invention, comprising nucleotides which are complementary to all or a portion of the nucleotides constituting the native mRNA, and which are capable of pairing with said mRNA.

The expression "antisense mRNA" means an RNA sequence which is complementary to a base sequence of a corresponding mRNA, which is complementary in the sense that each base (or the majority of the bases) in the antisense sequence (reading in the 3' to 5' direction) is capable of pairing with the corresponding base (G with C, A with U), in the mRNA sequence reading in the 5' to 3' direction.

A fifth subject according to the invention relates to a protein with the activity of the TOCB enzyme described by SEQ ID NO:2, or any modified protein of said TOCB enzyme, particularly by addition and/or deletion and/or substitution of one or more amino acids, or any fragment derived from the TOCB enzyme or from a modified sequence of the enzyme, said fragment or modified sequence having enzymatic activity which is equivalent to that of the TOCB enzyme.

A sixth subject according to the invention relates to a complex forms between an antisense mRNA defined in the fourth subject according to the invention, and an mRNA encoding a TOCB enzyme in the plant.

A seventh subject according to the invention is a recombinant DNA comprising a DNA sequence defined in the first subject according to the invention, said sequence being inserted into a heterologous sequence, said sequences transcribing all or a portion of an mRNA sequence encoding all or a portion of the TOCB enzyme, this enzyme having enzymatic activity which is equivalent to that of the TOCB enzyme of the plant.

According to the present invention, the expression "heterologous sequence" means any sequence which may be cut by enzymes, and which consequently serves to insert other sequences with diverse activities.

An eighth subject according to the invention is a recombinant DNA comprising a DNA sequence defined in the second subject according to the invention, said sequence being inserted into a heterologous sequence, said sequences transcribing all or a portion of an antisense mRNA sequence capable of pairing with an mRNA encoding a TOCB enzyme in the plant.

A ninth subject according to the invention is a recombinant DNA defined in the seventh or eighth subject according to the invention, comprising the elements required to control the expression of the inserted sequence, in particular a promoter sequence and a sequence for stopping the transcription of said sequences.

A tenth subject according to the invention relates to a vector for transforming plants, which is adapted to increase carotenoid biosynthesis, comprising all or a portion of the nucleotide sequence of SEQ ID NO:1 as defined in the first subject according to the invention, encoding all or a portion of an enzyme involved in carotenoid synthesis, represented by SEQ ID NO:2, preceded by an origin of replication of the transcription of the plants, such that the vector can generate mRNA in the plant cells.

An eleventh subject according to the invention relates to a vector for transforming plants, which is adapted to reduce or stop carotenoid biosynthesis, comprising all or a portion of the strand of the nucleotide sequence which is complementary to SEQ ID NO:1 as defined in the second subject according to the invention, preceded by an origin of replication of the transcription of the plants, such that the complementary strand transcribed can pair with the mRNA encoding the plant's TOCB enzyme involved in carotenoid synthesis.

The invention may thus be used to modify carotenoid synthesis, for example to increase or reduce, or even stop, the production of the colors associated with the dehydrogenation of phytoene. For example, the inhibition of the red color in fruit such as tomatoes, by transformation with a vector comprising an antisense sequence, gives a fruit with an attractive color close to yellow, for instance that of certain capsicums. Yellow tomatoes of this kind already exist, but the present invention provides a means for transferring the characteristic color into lines, without a prolonged reproduction program being necessary and as a result possibly giving rise to an impairment of other characteristics of the plant.

The increase in carotenoid synthesis by transformation with a vector comprising a sense sequence may make it possible to produce tomatoes of a more intense red color, which consumers may find more appetizing. The invention may also serve to introduce a red color into a plant, other than into the fruit. The increase in carotenoid synthesis in a plant may be carried out by inserting one or more functional copies of the complementary DNA gene, or the whole gene, under the control of a functional promoter into the plant cells.

The vectors for transforming plants to reduce or stop carotenoid synthesis, i.e. the antisense vectors, may be very short. In one preferred embodiment, homologous base sequences having a length of at least 10 bases will be selected. There is no theoretical upper limit to the base sequence; it may be as long as the mRNA produced by the plant. However, in one very preferential embodiment, sequences between 100 and 1000 bases long will be used.

It is known that the mutant plants in which the TOCB gene is inactive have a variegated appearance; the plants are green and white. An application of the antisense strategy is proposed, which is directed toward eliminating the production of mRNA and thus of the TOCB protein, which would be directed toward producing plants with variegated foliage such as, for example, ornamental plants, for instance Nicotiana or Petunia or any other ornamental plant, which lends itself to genetic transformation and which could receive an antisense construct for the purpose of preventing the production of the TOCB protein.

The DNA recombination products may be manufactured using standard techniques. For example, the DNA sequence to be transcribed may be obtained by treating a vector containing said sequence with restriction enzymes to cut out the appropriate segment. The transcription DNA sequence may also be generated by cyclizing and binding synthetic oligonucleotides or by using synthetic oligonucleotides in a PCR ("polymerase chain reaction") to generate restriction sites at each end. The DNA sequence is then cloned into a vector containing a start promoter sequence and a stop sequence. If it is desired to obtain an antisense DNA sequence, the cloning will be carried out so that the DNA sequence cut out is inverted relative to its orientation in the strand from which it was cut out.

In a recombination product expressing an antisense RNA, the strand which was initially the matrix strand becomes the coding strand, and vice versa. The recombination product will consequently transcribe an mRNA whose base sequence is complementary to all or a portion of the sequence of the mRNA for the enzyme. Consequently, the two RNA strands are complementary not only in their base sequences but also in their orientation (5' to 3').

In a recombination product which expresses a sense RNA, the matrix and the transcribed strands retain the orientation of the initial gene of the plant. The recombination products expressing sense RNA transcribe an mRNA having a base sequence which is totally or partially homologous with the sequence of the mRNA. In the recombination products expressing the functional enzyme, the whole coding region of the gene is linked to transcription control sequences capable of being expressed in the plant.

For example, the recombination products according to the present invention may be manufactured as described below. A suitable vector containing the desired base sequence for the transcription, in particular such as a DNA clone which is complementary to TOCB, is treated with restriction enzymes to cut the sequence. The DNA thus obtained is then cloned, in an inverted orientation if so desired, into a second vector containing the desired promoter sequence and the desired stop sequence. Among the suitable promoters, mentioned may be made of the promoter known as 35S of the CaMV virus as an example of a promoter considered as being constitutive; the promoter for the polygalacturonase gene of tomato (see Bird et al., 1998, Plant Molecular Biology, 11:651–662) as an example of a promoter involved in fruit regulation; or alternatively the promoter of the gene for the small subunit of ribulose bis-phosphate carboxylase, as an example of a promoter expressed in green tissues. The stop sequences comprise the NOS terminator of the nopaline synthase gene.

It may be advantageous to modify the enzymatic activity of the plant during only the growth and/or ripening of the fruit. The use of a constitutive promoter will tend to modify the level and activity of the enzyme in all the parts of the transformed plant, while the use of a promoter which is specific for a tissue will more selectively control the expression of the gene and will modify the activity, for example the coloration of the fruit. Consequently, by implementing the invention, for example in capsicums, it will be suitable to use a promoter which will allow the specific expression during the growth and/or ripening of the fruit. Finally, the sense or antisense RNA will, in this case, be produced only in the plant organs where it is desired for there to be an action. Among the specific promoters of the growth and/or ripening of fruit which may be used, mention may be made of the polygalacturonase stimulating promoter (international patent application published under No. WO-A-92/08798), the E8 promoter (Dieckman & Fiscer, 1998, EMBO, 7:3315–3320) and the fruit-specific 2A11 promoter (Pear et al., 1989, Plant Molecular biology, 13:639–651).

A twelfth subject according to the invention relates to a plant cell transformed with a vector defined in the tenth or eleventh subject according to the invention.

A person skilled in the art of plant genetic engineering is nowadays fully aware of the various techniques for obtaining genetically modified plants. It is known that the plant wall constitutes a natural mechanical barrier that is particularly effective against the penetration of any foreign matter into the cell and, in particular, against the penetration of DNA. The various specific techniques for introducing DNA into plant cells are, for example, the use of the bacterium *Agrobacterium tumefaciens*, the electroporation of protoplasts, the microinjection of naked DNA, the use of a biolistic or particle gun, or the transformation of protoplasts.

In order to be able to select the cells which have effectively been transformed, a marker gene is introduced, in addition to the gene encoding the desired character. A gene which imparts resistance to an antibiotic will preferably be selected. In this case, the cells are selected by culturing on a medium containing this antibiotic. Only the cells containing the resistance gene may multiply.. The presence of the gene of interest may also be confirmed by hybridization with DNA complementary to the DNA introduced.

The recombination product according to the invention is transferred into a target plant cell. The target plant cell may be a portion of a whole plant or may be an isolated cell or a portion of a tissue which may be regenerated inside a whole plant. The target plant cell may be chosen from any species of monocotyledon or dicotyledon plant. Suitable plants comprise any fruit-bearing plant, in particular such as tomatoes, mangoes, peaches, apples, pears, strawberries, bananas, melons, capsicums, pimentas, paprika, plants having foliage, flowers or any other organ in which it is desired to modify the carotenoid content.

The recombination products according to the invention may be used to transform any plant, using any technique that is suitable for transforming plants according to the invention. The cells of monocotyledon and dicotyledon plants may be transformed in various ways that are known to those skilled in the art. In most cases, the cells of these plants, particularly when they are cells of dicotyledon plants, may be cultured to generate a whole plant which reproduces thereafter to give rise to successive generations of genetically modified plants. Any process which is suitable for transforming plants may be used. For example, dicotyledon plants, such as tomato and melon, may be transformed using the *Agrobacterium* Ti plasmid. Such transformed plants may reproduce by crossing, or by cell or tissue culture.

A thirteenth subject according to the invention relates to a plant, or plant fragment, particularly a fruit, seed, petal or leaf, comprising cells defined according to the twelfth subject of the invention.

The plants or plant fragments that are genetically modified according to the invention with a vector comprising a sense sequence, in particular to increase the production of carotenoids, comprise a high level of vitamin A precursor relative to the normal level produced by the plant.

In addition to their role in the color of the plant, carotenoids also have a role of protecting plants against damage which may be brought about by high-intensity light. As a result, plants containing a higher level of these carotenoids by genetic modification may be of great interest for regions in which cultivation is carried out with large changes in temperature.

The genetically modified plants may have various colors, depending on whether the carotenoid synthesis has been increased or reduced. More particularly, the TOCB recombination products may be used to stimulate or inhibit the production of the colors associated with the carotenoids produced during the desaturation reactions, for example lycopene red, or product derivatives such as the yellow/orange color associated with beta-carotene. Stimulation of the production of beta-carotenes, with an overexpression sense recombination product, may make it possible to produce capsicums of yellow/orange color, or alternatively a color determined by a beta-carotene derivative such as a more intense red, due to the biosynthesis of capsorubin or capsanthine. The capsicums obtained will be found to be more appetizing by consumers.

As examples of genetically modified plants according to the present invention, mention will be made more particularly of fruit-bearing plants. The fruit of these plants may thus be made more appealing to consumers by stimulating or intensifying a specific color inside. As other plants which may be genetically modified, mention may be made of tubers such as radish, turnip and potato, and also cereals such as corn, wheat, barley and rice.

The genetically modified plants according to the invention may also contain other recombination products, for example recombination products having other effects, in particular on the ripening of fruits. For example, fruit having a more intense color, modified according to the present invention, may also contain recombination products, either which inhibit the production of certain enzymes such as polygalacturonase and pectin esterase, or which interfere with the production of ethylene. Fruit which contain these two types of recombination products may be produced, either by successive transformations, or by crossing two varieties which each contain one of the recombination products, followed by selecting, from the descendents, those which contain the two recombination products.

A fourteenth subject according to the invention relates to a process for modifying the production of carotenoids in a plant, either by increasing the production of carotenoids, or by reducing or inhibiting the production of carotenoids by the plant, relative to the normal content of carotenoids produced by the plant, said process comprising the transformation of cells of said plants to be transformed with a vector defined in the tenth and eleventh subject according to the invention.

A fifteenth subject according to the invention relates to a process for producing carotenoids in a plant cell, or eukaryotic or prokaryotic cell, said process comprising the transformation of cells of said plants, eukaryotic or prokaryotic cells to be transformed with a vector defined in the tenth subject according to the invention.

The beta-carotenes produced by a eukaryotic or prokaryotic organism expressing a recombination product encoding the TOCB enzyme, may be extracted in order to be used as a colorant, antioxidant or vitamin A precursor.

Finally, the invention also relates to a process for selecting compounds of herbicidal nature, in which said agent is placed in contact with cells or cell membranes, in particular cells of the invention, and a reduction in the consumption of oxygen by the membranes of said cells, which is associated with the inhibition of the terminal oxidase associated with carotenoid biosynthesis, is observed. Suitable techniques for making this observation are illustrated in particular in Example 6.

FIG. 1 shows the cDNA sequence (SEQ ID NO: 1) and the corresponding amino acid sequence (SEQ ID NO: 2) of TOCB. The N-terminal potential transit peptide of the chloroplast is underscored. The probable cleavage point is indicated by an asterisk (*). The open triangles indicate the position of the introns.

FIG. 2 shows the comparison between the TOCB protein (residues 111–299 of SEQ ID NO: 2) and the AOX protein of soybean (SEQ ID NO: 8). (+) indicates the similar amino acids. The amino acids shown in a box form part of the predicted transmembrane helix domains. The iron-binding moieties are overscored.

FIG. 3 shows the alignment of the amino acid sequences for tomato (T) (SEQ ID NO: 9), capsicum (P) (SEQ ID NO: 10) and Arabidopsis (A) (SEQ ID NO: 2) and the consensus sequence. In this consensus sequence, the conserved amino acids are indicated in upper letters and the relatively conserved amino acids are indicated in lowercase letters.

EXAMPLE 1

Figure 4A:
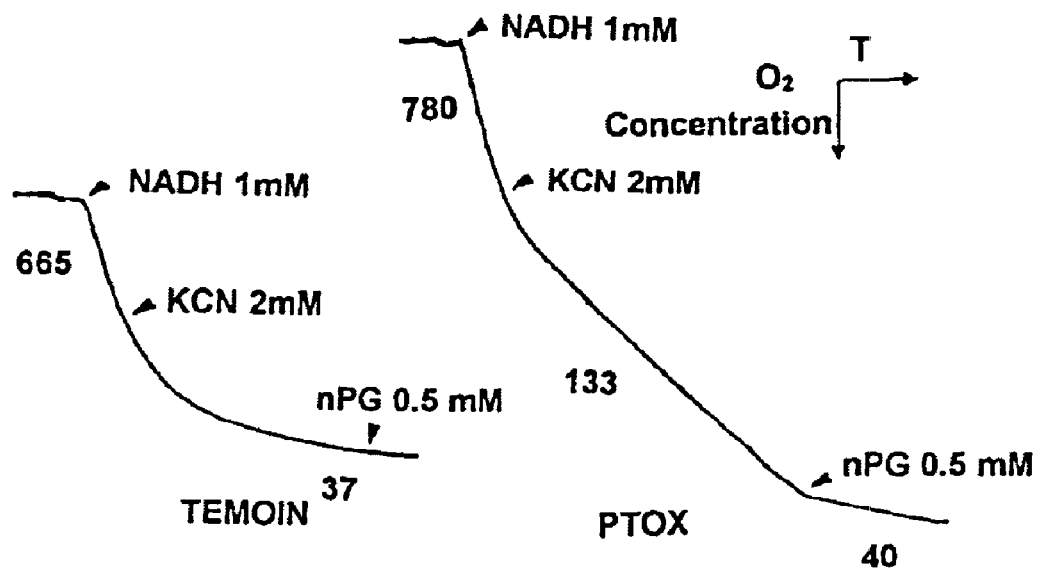
FIG. 4 represents the oxygen consumption in isolated *E. coli* cell membranes for control cells transformed with a cloning vector of the invention and for cells expressing the product of the "IMMUTANS" gene (plastid terminal oxidase).

Detail of the Cloning of the Locus Encoding the TOCB Protein

1—Isolation of the Mutant

Mutation was induced by using a transposon introduced into the genome of the plant *Arabidopsis thaliana* cultivar *landsberg-erecta*.

This technique is largely described in an article (Long, D., Martin, M., Sundberg, E., Swinburns, J., Puangsomlee P., and Coupland, G. (1993) The maize transposable element system Ac/Ds as a mutagen in Arabidosis: Identification of an albino mutation induced by Ds insertion. Pro. Natl. Science USA, 10, 10370–10374) and has been used by others in the laboratory of George Coupland at the John Innes Centre for Plant Science, Colney, Norwich, NR4 7UH, Nordwich [sic], Great Britain.

The transposition of the dissociator (Ds) transposable element used here was triggered by producing the transposase protein (or transposase of the activator element, Ac).

Among the descendents of a plant which has undergone the transposition of the element Ds, several plants having the albino mutant appearance, which differs from the wild-type plant by the absence of green pigmentation (chlorophyll), were identified. Plants of wild-type appearance but which transmit the mutation to their descendents were also identified. These plants are identified as heterozygotes, bearing the mutation on only one chromosome. The homozygous plants have a mutant phenotype and bear the mutation on the two homologous chromosomes.

2—Test of Binding of the Mutation to the Transposable Element Ds

This experiment was carried out with the aim of proving that the mutation observed is caused by the insertion of the element Ds into a gene which is required for correct functioning of the plant and for its wild-type appearance.

The transposable element, or transposon, Ds, is constructed so as to bear a gene for resistance to the antibiotic hygromycin (described in the preceding references). The descendents of 35 heterozygous plants which bear the albino mutation were grown on an agar medium containing a lethal dose of hygromycin; all the plants which bear the mutation are also hygromycin-resistant. The conclusion is drawn therefrom that the mutation is associated with the resistance gene borne by the transposon.

A portion of DNA from a plant resistant to the antibiotic hygromycin, adjacent to the transposon, was isolated. This was carried out according to the IPCR or inverse PCR method described in the preceding references.

By means of a "Southern blot" experiment, it was noted that the lines which bear the mutation have an alteration in the genomic DNA. This alteration is revealed when the portion of isolated DNA adjacent to the transposon is used as a "probe".

3—Isolation of the Gene

Using a method for screening a genomic DNA library, a clone was isolated containing a genomic DNA fragment which may contain the unaltered wild-type version of the interrupted gene in the mutant.

The DNA library screened was constructed. It is described in the publication by Whitelam, G. C., Johnson, E., Peng, J., Carol P., Anderson, M. L., Cowl, J. S. & Harberd, N. P. (1993) Phytochrome A null mutants of Arabidopsis display a wild-type phenotype in white light. The Plant Cell 5, 757–768.

The total sequence of a restriction fragment obtained by enzymatic digestion of the genomic DNA clone with the enzyme EcoR I was determined. The sequence obtained covers 3000 base pairs. Among these 3000 base pairs, a portion identical to the sequence of the border fragment isolated beforehand is found, confirming the identity between the isolated DNA and the gene interrupted with the transposon.

4—Isolation and Characterization of the Coding Sequence

A cDNA library was used, which is a commercial library sold by Clontech Laboratories, Inc. This is a cDNA library made from mRNAs extracted from *Arabidopsis thaliana*, transformed into cDNAs and then cloned into the plasmid vector pGAD10.

Using this cDNA data library, and according to the usual techniques, using the gene identified above as a probe, several clones containing a cDNA of about 1400 base pairs in size were isolated.

The total sequence of the cDNA was determined and showed that this cDNA is entirely within the genomic DNA fragment identified previously. The coding portion (or exons) and the noncoding portion (introns) of the gene were placed on the sequence of the gene. The gene bears 9 exons and 8 introns. The insertion of the transposon Ds was identified at the start of the second exon and thus interrupts the coding portion of the gene.

The cDNA sequence has a potential start codon followed by an open reading frame of 350 amino acids, encoding a potential protein of 39 kDa known as TOCB. A search for homology using the blastp program [(Altshul et al. (1997), Gapped BLAST and PSI-BLAST: a new generation of protein database search programs Nucleics Acids Res. 25, 3389–3402] revealed a low but significant homology with polypeptides belonging to the family of mitochondrial alternative oxidase or terminal oxidase (AOX) proteins. No other significant homology was found. The homology starts at amino acid 111 and shows 29% identity (45% similarity) with soybean oxidase. Despite the low identity with the AOX protein, a computer search for secondary structures and potential domains of biological significance revealed a structural similarity between the protein TOCB and AOX. Transmembrane helix domains found in AOX are located in similar positions on the peptide sequence of TOCB, suggesting a membrane location of TOCB and also a configuration similar to that of AOX in the membrane. Furthermore, an iron-binding moiety is conserved between TOCB and AOX. The alignment of the sequences between the proteins TOCB and AOX shows an insertion of 19 amino acids into the TOCB protein which corresponds to a portion of the exons 7 and 8.

The N-terminal sequence of the TOCB protein has the characteristics of a chloroplast transit peptide, which is rich in leucine, arginine and serine/threonine. A computer analysis of the transit peptide potential (psort software, Nakai and Kanehisa, 1992) suggested a possible target for TOCB in the thylakoid compartments of the chloroplast.

5—Identification of the Mutation

The appearance of the mutant is similar to that of a mutant already described in the literature: the "immutans" mutant, Wetzel C. M., Jiang C-Z., Meehan L. J., Voytas D. L., Rodermel S. R. (1994) Nuclear-organelle interactions: the immutans variegation mutant or Arabidopsis is plastid autonomous and impaired in carotenoid biosynthesis, Plant Journal 6, 161–175.

The "immutans" mutant (spotty allele, cf. preceding reference) was crossed with that which was isolated according to the invention. The descendents of the crossing is of mutant appearance, which is an expected result if the two mutations affect the same gene. It may thus be asserted that the gene identified corresponds to the wild-type version of the IMMUTANS locus and that the mutant obtained bears an interrupted version of the gene, the product of which is thus inactive.

The first subject of the present invention thus differs from the above mutant in that it encodes a protein whose enzymatic activity is identical or equivalent to that of TOCB, while the product encoded by "immutans" has no activity.

EXAMPLE 2

Construction of a Vector of the Invention by Introduction of cDNA Encoding Capsicum TOCB into a Plant Expression Vector The vector pBI121 (sold by Clontech Laboratories, Inc.) is a vector that is suitable for this construction.

It comprises a T-DNA region which the bacterium *Agrobacterium tumefaciens* can transfer into the plant genome.

This T-DNA region comprises, inter alia, a constitutive promoter (the promoter known as 35S from CaMV virus), the GUS gene followed by the NOS terminator (of the nopaline synthase gene). As the GUS gene is of no interest in the invention, it is replaced with a cDNA encoding TOCB. This cDNA will thus be placed under the control of the 35S promoter and the NOS terminator.

Any other constitutive or nonconstitutive promoter (in the latter case, it will need to be specific for the organ whose properties it is desired to modify) and any other terminator may also be used.

A cDNA encoding TOCB was initially subcloned into the NotI restriction site of the bacterial plasmid pBluescriptKS: it was thus flanked by a 5' BamHI cleavage site and a 3' SacI cleavage site.

This cDNA is excized from the plasmid pBluescriptKS with the restriction enzymes BamHI and SacI. This BamHI-SacI fragment is inserted into the vector pBI121 which is itself cleaved with these enzymes: the BamHI site is at the 3' end of the 35S promoter and at the 5' end of the GUS gene, and the SacI site is at the 3' end of the GUS gene and at the 5' end of the NOS terminator.

After ligation, the derivatives of the vector pBI121 in which the cDNA encoding TOCB (that is to say without intron) has replaced the GUS gene, are selected.

EXAMPLE 3

Transformation of a Plant Cell to Obtain a Transformed Cell of the Invention

The plant transformation vector derived from pBI121 obtained in Example 2 is introduced into the strain of Agrobacterium LBA4404 by electroporation. The recombinant strain is selected in the presence of 50 µg/ml of kanamycin.

This transformed strain of Agrobacterium is used for the transformation of plant cells, for example tobacco cells.

The technique used to do this, which may be replaced by any other transformation technique, is that of infecting foliar disks of tobacco plantlets cultivated in vitro. The transformed plant cells are selected in the presence of kanamycin. Agrobacterium is eliminated by the antibiotic cefotaxime. The foliar disks are cultivated on plant culture medium in the presence of plant hormones (auxin and cytokinins) which promote the growth of cals. The cals derived from the growth of the transformed cells are used for the regeneration of whole plants by the conventional techniques. For example, the cals are transferred onto plant culture medium in the presence of cytokinin to induce the formation of shoots. These shoots are then cut up and transferred onto hormone-free plant culture medium in order to regenerate roots. The antibiotics kanamycin (to select for the growth of transformed tissues) and cefotaxime (to completely eliminate Agrobacterium) are maintained throughout these culturing phases.

The transformed plants are placed in sterile culture in the presence of kanamycin and cefotaxime and are then transferred to soil and cultivated in a greenhouse until the seeds are harvested. The presence of the transgene was confirmed by hybridization of the genomic DNA of these plants with a specific probe derived from the transformation vector used.

EXAMPLE 4

Cloning and Characterization of cDNA of Capsicum and Tomato Fruit Corresponding to the Terminal Oxidase Associated with Carotenoid Biosynthesis (TOCB) Enzyme The "immutans" cDNA portion of Arabidopsis encoding the mature TOCB peptide was used as a probe to search for a cDNA library for green pepper or red pepper under nonstringent conditions. All the positive clones which were analyzed appeared to be derived from the same gene, as suggested by the identical sequences observed in the nontranslated 3' region. The DNA sequence of the whole clone is presented in the sequence listing under the identifier SEQ ID NO:3. The deduced amino acid sequence is presented in the sequence listing under the identifier SEQ ID NO:4. The capsicum cDNA was then used to isolate the corresponding cDNA from a red tomato cDNA library (SEQ ID NO:5).

FIG. 3 shows the comparison between the abovementioned deduced amino acid sequence and the sequences of capsicum and Arabidopsis TOCB.

The transit peptides used for targeting in the plastids revealed a sequence similarity, with the exception of the N-terminal region and of the region close to the assumed cleavage site (ATR/Q-AT). However, the mature TOCB polypeptides share a strong sequence similarity, which means that they have the same properties.

An alignment of the TOCB sequences also revealed the presence of two conserved potential transmembrane domains, separated by a highly conserved hydrophilic segment. The N-terminal domain is essentially hydrophilic and contains a long weakly conserved amino acid segment. The C-terminal domain is also mainly hydrophilic and contains a conserved moiety (EAEH) which matches a putative iron-binding site (ExxH). In addition, the region contains 6 cysteine residues that are conserved in TOCB, while the rest of the polypeptide lacks cysteine residues. Some of these cysteine residues may be involved in the covalent dimerization of the protein.

EXAMPLE 5

Expression of the TOCB Genes During Ripening of the Fruit in Capsicums and Tomatoes In order to define the mechanisms of expression of the TOCB genes, the total RNA was extracted from fruit at different stages of ripening. The expression mechanism was determined by reverse transcription of the total RNA, followed by a polymerase chain reaction (RT-PCR).

The TOCB gene is expressed during the growth and ripening of the capsicum fruit. In addition, it has an expression mechanism which is similar to that of genes encoding carotenoid desaturases, that is to say phytocene desaturase and zeta-carotene desaturase. An increase in the level of transcription is observed between the unripe green stage and the ripe green stage (fruit of an adult size), followed by another increase between the ripe green stage and the degradation stage (early visible signs of a color change). The level of transcription then remains fairly constant (with a slight decrease during the reddening step).

The TOCB gene is also expressed during the growth and ripening of fruit in tomatoes. In tomatoes, there is also an expression mechanism which is similar to that of the genes encoding carotenoid desaturases (phytoene desaturase and zeta-carotene desaturase). An increase in the level of transcription is observed between the unripe green stage and the ripe green stage (adult-sized fruit), followed by another, greater increase between the ripe green stage and the degradation stage.

When the imprint of the protein of the capsicum and tomato fruit was desired, using antibodies directed against TOCB, this polypeptide was found at various stages of development of the fruit. These tests demonstrated an increase in the level of the TOCB protein, from the ripe green stage to the degradation stage. This level of protein remained high throughout the ripening of the fruit.

These results demonstrate that the TOCB genes are expressed and that the TOCB protein is present in the fruit. In a manner similar to that of the structural enzymes involved in the desaturation of are accumulated during the ripening when the carotenoid biosynthesis is increased.

The results presented in the description reveal that TOCB is an element of the carotenoid biosynthesis system.

It may be envisaged to use the TOCB protein to modify carotenoid biosynthesis, in particular in plant tissues or cells or in bacteria which have an inefficient or poorly efficient carotenoid biosynthesis system. TOCB may be produced at the same time as the structural enzymes of carotenoid biosynthesis to increase the efficacy of the production of carotenoids.

EXAMPLE 6

Catalytic Properties of TOCB Analyzed After its Expression in *E. coli*

A synthetic product consisting of the region encoding the mature TOCB polypeptide from Arabidopsis was inserted into a prokaryotic expression vector (such as pQE31, sold by QIAGEN, it being understood that any other vector would give identical results).

The coding region intended to be inserted into the expression vector may be obtained by cleavage using restriction enzymes which act close to the codons corresponding to the site of cleavage of the transit peptide.

Alternatively, an amplification by PCR of the coding region may be carried out. The following oligonucleotides will advantageously be used to amplify the sequence of Arabidopsis TOCB:

5'-GCAACGATTTTGCAAGACG-3' (SEQ ID NO: 6) and

5'-TTAACTTGTAATGGATTTCTTGAG-3' (SEQ ID NO: 7).

Other assembly products comprising the region encoding TOCB in other species (such as capsicum or tomato) may also be used.

These plasmids may be introduced into E. coli cells according to conventional techniques. In order to obtain the recombinant protein in E. coli, the cells are cultured under the following conditions: 10 ml of an overnight preculture in a rich medium are deposited in 300 ml of M9 medium ($Na_2HPO_4$ 34 mM, $KH_2PO_4$ .22 mM, $NH_4Cl$ 18 mM, NaCl 8.5 mM, $MgSO_4$ 1 mM, $CaCl_2$ 0.1 mM, thiamine 1 mM) containing 0.2% of glycerol and the supply of antibiotic required to stop the growth of the cells which have lost the plasmid. The growth of the bacteria is continued at 37° C. with vigorous agitation up to the half-exponential growth phase, preferably until an optical density of 0.3 at 600 nm is read.

After inducing this chimeric gene with the inducer IPTG and adding 1 mg/l of $FeSO_4$, the culture is maintained at 25° C. with vigorous agitation for 3 hours. The cells are then harvested by centrifugation at 4° C., washed with 10 mM $MgCl_2$, 0.75M sucrose, 20 mM Tris-HCl, at pH 7.5, and centrifuged again. The cells are then suspended in 0.75M sucrose, 20 mM Tris-HCl, at pH 7.5, and lysed by addition of lysozyme (0.2 mg/ml) and EDTA (25 mM) at 30° C. for 30 minutes, and then subjected to an osmotic shock by addition of two volumes of water, after which they are treated with ultrasound at 0° C. A standard centrifugation in a centrifuge at slow speed makes it possible to remove the nonlysed cells and the debris. A high-speed centrifugation (for example in a Beckman 50 Ti rotor at 40000 rpm) at 4° C. produces a membrane which is suspended in 0.75M sucrose, 20 mM Tris-HCl, at pH 7.5, and maintained at 4° C.

To test the enzymatic activity of the TOCB, the consumption of oxygen by the resulting membranes is measured using a standard oxygen electrode and is expressed in nmol of $O_2$ consumed per minute and per gram of protein.

Figure 4B:
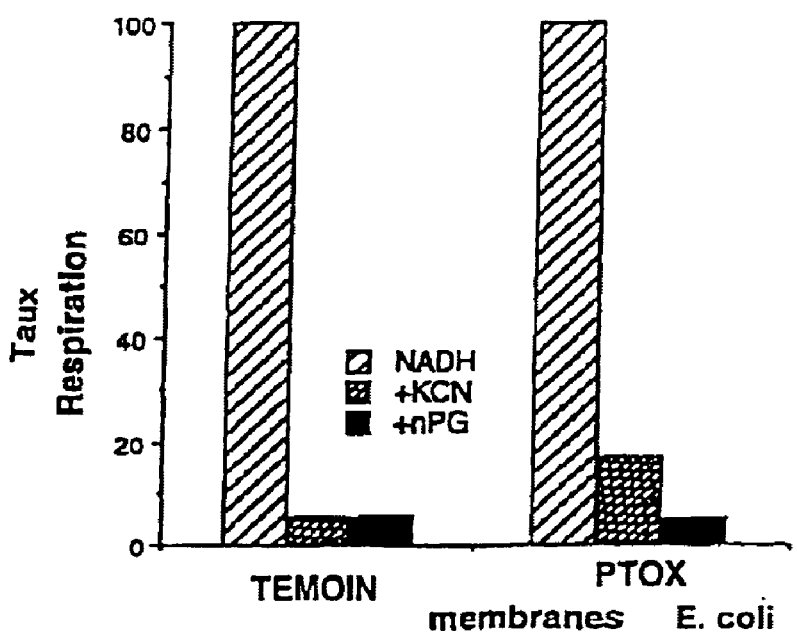

As shown in FIG. 4, the addition of NADH induces the consumption of oxygen both in the control membrane (transformed with the cloning vector) and in the membrane containing the TOCB. This oxygen consumption increases when 0.2 mM plastoquinone is added. The addition of KCN greatly inhibits the oxygen consumption in the control membranes. In the membranes containing TOCB, a high cyanide-resistant oxygen consumption is observed. This reflects the plastoquinol:oxygen oxidoreductase activity of the TOCB, which activity may be inhibited by adding 0.5 mM n-propyl gallate (nPG). The addition of nPG (0.5 mM) to the control membrane before KCN does not produce an effect, indicating that the compound does not interfere with the normal flow of electrons in the E. coli membranes (FIG. 4).

This test may be used to study the inhibitory power of a compound on TOCB activity. Thus, an inhibitor may be controlled when it has no effect on the endogenous respiratory chain of E. coli, in particular on the complex I of the chain which oxidizes NADH. Nevertheless, if such is the case, NADH may be replaced with succinate as an electron donor without passing via the complex I. Any inhibitor of TOCB activity may be tested on suitable plants, by watering the soil, adding a culture medium and applying directly to the leaves, with respect to the inhibition of carotenoid biosynthesis, resulting in bleaching, and may thus find an application as a herbicide.

The test described may be modified to carry out a large-scale screening of inhibitors of TOCB activity, and their application as herbicides. In this case, measurement of the oxygen consumption using an oxygen electrode will preferably be replaced with another method of measurement.

The oxidase activity of TOCB may be determined by measuring the consumption of NADH during the reaction, for example by spectrophotometry, by measuring the absorbance at 340 nm. The consumption of NADH and the production of NAD during the test should result in a decrease in the absorbance at 340 nm. Alternatively, any specific coloration of NAD or of NADH may be used to monitor changes in NAD or NADH during the test.

If succinate is used as an electron donor in the test, the respiratory activity of the bacterial membranes will result in the oxidation of the succinate to fumarate. In this case, the activity of the TOCB may be monitored in the presence of KCN, by measuring the concentrations of succinate and fumarate which change during the test.

According to another possibility, an artificial electron donor may be used. An example of this is phenazine metasulfate (PMS). It may be oxidized by the succinate dehydrogenase of the bacterial membranes; it is colorless in the reduced form and yellow in the oxidized form.

Samples of bacterial membrane containing TOCB oxidize PMS in the presence of KCN. An inhibitor of TOCB activity will prevent the appearance of the yellow color due to the oxidation of the PMS. This test, which is simple to perform, may be carried out in multi-well plates, allowing a bulk screening of molecules capable of inhibiting the activity of TOCB to be performed.

What is claimed is:

1. A process for modifying the production of carotenoids in a plant, by increasing the production of carotenoids relative to the normal content of carotenoids produced by the plant, said process comprising transformation of cells of said plant with a vector comprising:
   (1) a nucleotide sequence encoding an enzyme having terminal oxidase activity involved in carotenoid biosynthesis, said enzyme comprising SEQ ID NO: 2, or
   (2) a nucleotide sequence having at least 70% sequence identity to SEQ ID NO: 1 and encoding an enzyme having terminal oxidase activity involved in carotenoid biosynthesis,
   wherein said nucleotide sequence is operably linked to a promoter, such that the vector can generate mRNA in the plant cells, and the production of carotenoids in said plant is increased.

2. A process for producing carotenoids in a plant cell, or eukaryotic or prokaryotic cell, said process comprising transformation of at least one plant, eukaryotic or prokaryotic cell with a vector comprising:
   (1) a nucleotide sequence encoding an enzyme having terminal oxidase activity involved in carotenoid biosynthesis, said enzyme comprising SEQ ID NO: 2, or
   (2) a nucleotide sequence having at least 70% sequence identity to SEQ ID NO: 1 and encoding an enzyme having terminal oxidase activity involved in carotenoid biosynthesis,
   wherein said nucleotide sequence is operably linked to a promoter, such that the vector can generate mRNA in said at least one cell, and the production of carotenoids in said plant, eukaryotic or prokaryotic cell is increased.

3. The process according to claim 1, wherein said vector comprises a nucleotide sequence encoding SEQ ID NO: 2.

4. The process according to claim 2, wherein said vector comprises a nucleotide sequence encoding SEQ ID NO: 2.

5. The process according to claim 1, wherein said vector comprises a nucleotide sequence having at least 80% sequence identity to SEQ ID NO: 1 and encoding an enzyme having terminal oxidase activity involved in carotenoid biosynthesis.

6. The process according to claim 2, wherein said vector comprises a nucleotide sequence having at least 80% sequence identity to SEQ ID NO: 1 and encoding an enzyme having terminal oxidase activity involved in carotenoid biosynthesis.

\* \* \* \* \*

SEQUENCE LISTING

<160> NUMBER OF SEQ ID NOS: 10

<210> SEQ ID NO 1
<211> LENGTH: 1396
<212> TYPE: DNA
<213> ORGANISM: Arabidopsis thaliana

<400> SEQUENCE: 1

-continued

```
ccgctcacat tgggattcgt cattcttctt ctaaaacccg caaaatttct ccatttctac      60
caaaaatatc caacttttac ttttctttcc tgtgaaatta tctgctcaaa tctttggttc     120
ctgacggaga tggcggcgat tcaggcatc tcctctggta cgttgacgat tcacggcct       180
ttggttactc ttcgacgctc tagagccgcc gtttcgtaca gctcctctca ccgattgctt    240
catcatcttc ctctctcttc tcgtcgtctg ctattaagga acaatcatcg agtccaagca    300
acgattttgc aagacgatga agagaaagtg gtggtggagg aatcgtttaa agccgagact    360
tctactggta cagaaccact tgaggagcca aatatgagtt cttcttcaac tagtgctttt    420
gagacatgga tcatcaagct tgagcaagga gtgaatgttt tccttacaga ctcggttatt    480
aagatacttg acactttgta tcgtgaccga acatatgcaa ggttctttgt tcttgagaca    540
attgctagag tgccttattt tgcgtttatg tctgtgctac atatgtatga gacctttggt    600
tggtggagga gagcagatta tttgaaagta cactttgctg agagctggaa tgaaatgcat    660
cacttgctca taatggaaga attgggtgga aattcttggt ggtttgatcg ttttctggct    720
cagcacatag caaccttcta ctacttcatg acagtgttct tgtatatctt aagccctaga    780
atggcatatc acttttcgga atgtgtggag agtcatgcat atgagactta tgataaattt    840
ctcaaggcca gtggagagga gttgaagaat atgcctgcac cggatatcgc agtaaaatac    900
tatacgggag gtgacttgta cttatttgat gagttccaaa catcaagaac tcccaatact    960
cgaagaccag taatagaaaa tctatacgat gtgtttgtga acataagaga tgatgaagca   1020
gaacactgca agacaatgag agcttgtcag actctaggca gtctgcgttc tccacactcc   1080
attttagatg atgatgatac tgaagaagaa tcagggtgtg ttgttcctga ggaggctcat   1140
tgcgaaggta ttgtagactg cctcaagaaa tccattacaa gttaataaat tagaaagtaa   1200
actaaaaaag attattttgta tcagctcatg aacaatagat ataatcccat atacttggga   1260
ataaaggaat aatgtgaaat tcccatcgtt gtgctagtgt gtgagagaat caaatacccct   1320
aatgatgtaa atgtactttg atgagcttaa gtcgttgtag accatttatat caaaaaaaaa    1380
aaaaaaaaaa aaaaaa                                                     1396
```

<210> SEQ ID NO 2
<211> LENGTH: 351
<212> TYPE: PRT
<213> ORGANISM: Arabidopsis thaliana

<400> SEQUENCE: 2

```
Met Ala Ala Ile Ser Gly Ile Ser Ser Gly Thr Leu Thr Ile Ser Arg
1               5                   10                  15

Pro Leu Val Thr Leu Arg Arg Ser Arg Ala Ala Val Ser Tyr Ser Ser
            20                  25                  30

Ser His Arg Leu Leu His His Leu Pro Leu Ser Ser Arg Arg Leu Leu
        35                  40                  45

Leu Arg Asn Asn His Arg Val Gln Ala Thr Ile Leu Gln Asp Asp Glu
    50                  55                  60

Glu Lys Val Val Val Glu Ser Phe Lys Ala Glu Thr Ser Thr Gly
65                  70                  75                  80

Thr Glu Pro Leu Glu Glu Pro Asn Met Ser Ser Ser Thr Ser Ala
                85                  90                  95

Phe Glu Thr Trp Ile Ile Lys Leu Glu Gln Gly Val Asn Val Phe Leu
            100                 105                 110

Thr Asp Ser Val Ile Lys Ile Leu Asp Thr Leu Tyr Arg Asp Arg Thr
```

```
                    115                 120                 125
Tyr Ala Arg Phe Phe Val Leu Glu Thr Ile Ala Arg Val Pro Tyr Phe
    130                 135                 140
Ala Phe Met Ser Val Leu His Met Tyr Glu Thr Phe Gly Trp Trp Arg
145                 150                 155                 160
Arg Ala Asp Tyr Leu Lys Val His Phe Ala Glu Ser Trp Asn Glu Met
                165                 170                 175
His His Leu Leu Ile Met Glu Glu Leu Gly Gly Asn Ser Trp Trp Phe
            180                 185                 190
Asp Arg Phe Leu Ala Gln His Ile Ala Thr Phe Tyr Tyr Phe Met Thr
        195                 200                 205
Val Phe Leu Tyr Ile Leu Ser Pro Arg Met Ala Tyr His Phe Ser Glu
    210                 215                 220
Cys Val Glu Ser His Ala Tyr Glu Thr Tyr Asp Lys Phe Leu Lys Ala
225                 230                 235                 240
Ser Gly Glu Glu Leu Lys Asn Met Pro Ala Pro Asp Ile Ala Val Lys
                245                 250                 255
Tyr Tyr Thr Gly Gly Asp Leu Tyr Leu Phe Asp Glu Phe Gln Thr Ser
            260                 265                 270
Arg Thr Pro Asn Thr Arg Arg Pro Val Ile Glu Asn Leu Tyr Asp Val
        275                 280                 285
Phe Val Asn Ile Arg Asp Asp Glu Ala Glu His Cys Lys Thr Met Arg
    290                 295                 300
Ala Cys Gln Thr Leu Gly Ser Leu Arg Ser Pro His Ser Ile Leu Asp
305                 310                 315                 320
Asp Asp Asp Thr Glu Glu Glu Ser Gly Cys Val Val Pro Glu Glu Ala
                325                 330                 335
His Cys Glu Gly Ile Val Asp Cys Leu Lys Lys Ser Ile Thr Ser
            340                 345                 350

<210> SEQ ID NO 3
<211> LENGTH: 1387
<212> TYPE: DNA
<213> ORGANISM: capsicum

<400> SEQUENCE: 3
ccacgcgtcc gataaaaaaa tcaagaatgg cgatttccat atctgctatg agttttcgaa        60
cttcagtttc ttcttcatat tcagcatttt tgtgcaattc caagaaccca ttttgtttga      120
attctctatt ttcacttagg aattctcata gaacttttca gccttcgtta tcaaggaaat      180
caagtagagt tcgagcaacg ttgttaaaag agaatgaaga agaagtggtt gtggagaaat      240
cttttgcacc taagagtttt cctggtaatg tgggagggggg aaataatggg gagccacccg     300
ataattcatc ctcgaacggt ctggagaaat gggttataaa gattgagcag tctgtaaata     360
tctttctcac ggattcagtg ataaagattc ttgacacttt gtatcacgac cgacactatg     420
cgaggttttt cgttctggaa acaattgcaa gagttcctta ttttgcattt atatctgttc     480
ttcacttgta cgagagcttt ggttggtgga cgagcagaa ttatctgaag gtgcattttg      540
ccgagagctg gaatgagatg caccatttac tcattatgga ggaattaggt ggaaatgctt      600
ggtggtttga ccgattcctt gcgcaacata ttgctgtatt ctattatttc atgacagtct      660
cgatgtatgc tttgagcccg agaatggcat atcatttctc tgaatgtgtg gagcaccatg     720
catacgagac ttcgagataaa ttcatcaagg atcaagaagc ggaattgaag aaattgcccg     780
ctccaaagat tgcagtgagc tactacaccg gaggtgactt gtatttgttc gatgagtttc     840
```

-continued

```
aaacatcacg agagcctaat actcgaaggc caaaaataga taatctgtac gacgtattca      900
tgaacatcag agatgacgaa gcagagcatt gtaagacaat gaaagcgtgt caaacccatg      960
ggagcctccg ctcccctcac acaaatccat gcgatgagtc tgaagacgat ccaggttgtt     1020
cagtgcctca ggccgattgt gtaggtatcg tggattgtat aacgaaatct gtcgctgatc     1080
ctaacgtcgg cagaaggtag ggaaaggaaa aacgcagaac gaaactatac atgtatatac     1140
cagtacagcc aaatatacaa gaaatataca tacatattgt atcttttact ctctgaggaa     1200
gagcttgtca aattgcccaa aaaatgggta ggcacttggt tttgttttca cctttcaata     1260
atttgtacta aactatgaac aaatttgctc cggcacacta caactccata ggggtcctgt     1320
tacgcttctg aactaaattt taacatattt ttgtcaacct tctcagcaaa aaaaaaaaa     1380 aaaaaaa                                                               1387
```

<210> SEQ ID NO 4
<211> LENGTH: 357
<212> TYPE: PRT
<213> ORGANISM: capsicum

<400> SEQUENCE: 4

```
Met Ala Ile Ser Ile Ser Ala Met Ser Phe Arg Thr Ser Val Ser Ser
1               5                   10                  15

Ser Tyr Ser Ala Phe Leu Cys Asn Ser Lys Asn Pro Phe Cys Leu Asn
            20                  25                  30

Ser Leu Phe Ser Leu Arg Asn Ser His Arg Thr Phe Gln Pro Ser Leu
        35                  40                  45

Ser Arg Lys Ser Ser Arg Val Arg Ala Thr Leu Leu Lys Glu Asn Glu
    50                  55                  60

Glu Glu Val Val Val Glu Lys Ser Phe Ala Pro Lys Ser Phe Pro Gly
65                  70                  75                  80

Asn Val Gly Gly Gly Asn Asn Gly Glu Pro Pro Asp Asn Ser Ser Ser
                85                  90                  95

Asn Gly Leu Glu Lys Trp Val Ile Lys Ile Glu Gln Ser Val Asn Ile
            100                 105                 110

Phe Leu Thr Asp Ser Val Ile Lys Ile Leu Asp Thr Leu Tyr His Asp
        115                 120                 125

Arg His Tyr Ala Arg Phe Phe Val Leu Glu Thr Ile Ala Arg Val Pro
    130                 135                 140

Tyr Phe Ala Phe Ile Ser Val Leu His Leu Tyr Glu Ser Phe Gly Trp
145                 150                 155                 160

Trp Arg Arg Ala Asp Tyr Leu Lys Val His Phe Ala Glu Ser Trp Asn
                165                 170                 175

Glu Met His His Leu Leu Ile Met Glu Glu Leu Gly Gly Asn Ala Trp
            180                 185                 190

Trp Phe Asp Arg Phe Leu Ala Gln His Ile Ala Val Phe Tyr Tyr Phe
        195                 200                 205

Met Thr Val Ser Met Tyr Ala Leu Ser Pro Arg Met Ala Tyr His Phe
    210                 215                 220

Ser Glu Cys Val Glu His His Ala Tyr Glu Thr Tyr Asp Lys Phe Ile
225                 230                 235                 240

Lys Asp Gln Glu Ala Glu Leu Lys Lys Leu Pro Ala Pro Lys Ile Ala
                245                 250                 255

Val Ser Tyr Tyr Thr Gly Gly Asp Leu Tyr Leu Phe Asp Glu Phe Gln
            260                 265                 270
```

```
Thr Ser Arg Glu Pro Asn Thr Arg Arg Pro Lys Ile Asp Asn Leu Tyr
        275                 280                 285
Asp Val Phe Met Asn Ile Arg Asp Asp Glu Ala Glu His Cys Lys Thr
        290                 295                 300
Met Lys Ala Cys Gln Thr His Gly Ser Leu Arg Ser Pro His Thr Asn
305                 310                 315                 320
Pro Cys Asp Glu Ser Glu Asp Pro Gly Cys Ser Val Pro Gln Ala
                325                 330                 335
Asp Cys Val Gly Ile Val Asp Cys Ile Thr Lys Ser Val Ala Asp Pro
                340                 345                 350
Asn Val Gly Arg Arg
        355

<210> SEQ ID NO 5
<211> LENGTH: 1284
<212> TYPE: DNA
<213> ORGANISM: tomato

<400> SEQUENCE: 5
gaattcggca cgagcggcac gagcagaaaa ctaacaactt tcccactttg gaattttctt      60
taccttacct aagaagggta ttaatttgat tcttgtggga aggaagaagg atcaagaatg     120 gcgattcga tttctgctat gagttttgga acctcagttt cttcatattc ttgttttaga     180
gctaggagtt ttgagaagtc atcagtttta tgcaattccc agaacccatg tcggtttaat     240 tctgttttc cgattcggaa atctgatggg gcttcacggt gttctgtttc taggaaatca     300
tgtagagttc gagcaacgtt gttacaagag aatgaagaag aagtggttgt ggagaaatct     360
tttgcaccta agagttttcc tgataacgtg ggagggggaa gtaatgggaa gccaccagat     420
gattcatcct ctaacggtct agagaaatgg gttataaagc ttgagcagtc tgtaaatatc     480
ttactcacgg attcagtgat aaagattctt gacactttgt atcacaaccg aaactatgcg     540 aggtttttg ttctggaaac aattgcaagg gttccttatt ttgcatttat atcggttctt     600
cacatgtatg agagctttgg ctggtggaga agggcagatt atatgaaagt gcatttgct      660 gaaagctgga atgagatgca ccatttgctc attatggaag aattagggg aaatgcttgg     720 tggtttgatc gatttcttgc acaacatata gctatattct attatttcat gacagtcttg     780
atgtatgctt tgagcccgag aatggcatat catttctctg aatgtgtgga gagccatgca     840
tacgagactc acgataaatt catcaaggat caaggagagg aattgaagaa tttgcccgct     900
ccaaagattg cagtggacta ctacacggga ggtgacttat atttatttga tgagtttcaa     960
acttcacgag agcctaatac tcgaagacca aaaatagata atctctatga cgtattcatg    1020
aacattagag atgacgaagc agagcattgt aaaacgatga agcctgtca aactcacggg      1080 agccttcgtt ctccacacac agatccatgc gatgattctg aagatgatac agggtgttcc    1140
gtacctcaag ctgattgtat aggtatcgtg gattgtataa agaagtcagt caccgatact    1200
caagtaacca aaaggtagga aaggaaaaa cgcggacaaa ctatacttgt atatactagt    1260
atagacaaaa aaaaaaaaaa aaaa                                          1284

<210> SEQ ID NO 6
<211> LENGTH: 19
<212> TYPE: DNA
<213> ORGANISM: Artificial
<220> FEATURE:
<223> OTHER INFORMATION: PCR primer
```

-continued

```
<400> SEQUENCE: 6
gcaacgattt tgcaagacg                                                    19

<210> SEQ ID NO 7
<211> LENGTH: 24
<212> TYPE: DNA
<213> ORGANISM: Artificial
<220> FEATURE:
<223> OTHER INFORMATION: PCR primer

<400> SEQUENCE: 7
ttaacttgta atggatttct tgag                                              24

<210> SEQ ID NO 8
<211> LENGTH: 171
<212> TYPE: PRT
<213> ORGANISM: soybean

<400> SEQUENCE: 8

Tyr Arg Thr Val Lys Leu Leu Arg Ile Pro Thr Asp Leu Phe Phe Lys
1               5                  10                  15

Arg Arg Tyr Gly Cys Arg Ala Met Met Leu Glu Thr Val Ala Ala Val
            20                  25                  30

Pro Gly Met Val Gly Met Leu Leu His Leu Arg Ser Leu Arg Lys
        35                  40                  45

Phe Gln Gln Ser Gly Gly Trp Ile Lys Ala Leu Leu Glu Glu Ala Glu
    50                  55                  60

Asn Glu Arg Met His Leu Met Thr Met Val Glu Leu Val Lys Pro Lys
65                  70                  75                  80

Trp Tyr Glu Arg Leu Leu Val Leu Ala Val Gln Gly Val Phe Phe Asn
                85                  90                  95

Ala Phe Phe Val Leu Tyr Ile Leu Ser Pro Lys Val Ala His Arg Ile
            100                 105                 110

Val Gly Tyr Leu Glu Glu Glu Ala Ile His Ser Tyr Thr Glu Tyr Leu
        115                 120                 125

Lys Asp Leu Glu Ser Gly Ala Ile Glu Asn Val Pro Ala Pro Ala Ile
    130                 135                 140

Ala Ile Asp Tyr Trp Arg Leu Pro Lys Asp Ala Arg Leu Lys Asp Val
145                 150                 155                 160

Ile Thr Val Ile Arg Ala Asp Glu Ala His His
                165                 170

<210> SEQ ID NO 9
<211> LENGTH: 366
<212> TYPE: PRT
<213> ORGANISM: tomato

<400> SEQUENCE: 9

Met Ala Ile Ser Ile Ser Ala Met Ser Phe Gly Thr Ser Val Ser Ser
1               5                  10                  15

Tyr Ser Cys Phe Arg Ala Arg Ser Phe Glu Lys Ser Ser Val Leu Cys
            20                  25                  30

Asn Ser Gln Asn Pro Cys Arg Phe Asn Ser Val Phe Pro Ile Arg Lys
        35                  40                  45

Ser Asp Gly Ala Ser Arg Cys Ser Val Ser Arg Lys Ser Cys Arg Val
    50                  55                  60

Arg Ala Thr Leu Leu Gln Glu Asn Glu Glu Val Val Val Glu Lys
65                  70                  75                  80
```

Ser Phe Ala Pro Lys Ser Phe Pro Asp Asn Val Gly Gly Ser Asn
                85                  90                  95

Gly Lys Pro Pro Asp Ser Ser Asn Gly Leu Glu Lys Trp Val
            100                 105                 110

Ile Lys Leu Glu Gln Ser Val Asn Ile Leu Thr Asp Ser Val Ile
            115                 120                 125

Lys Ile Leu Asp Thr Leu Tyr His Asn Arg Asn Tyr Ala Arg Phe Phe
    130                 135                 140

Val Leu Glu Thr Ile Ala Arg Val Pro Tyr Phe Ala Phe Ile Ser Val
145                 150                 155                 160

Leu His Met Tyr Glu Ser Phe Gly Trp Trp Arg Arg Ala Asp Tyr Met
                165                 170                 175

Lys Val His Phe Ala Glu Ser Trp Asn Glu Met His His Leu Leu Ile
                180                 185                 190

Met Glu Glu Leu Gly Gly Asn Ala Trp Trp Phe Asp Arg Phe Leu Ala
                195                 200                 205

Gln His Ile Ala Ile Phe Tyr Tyr Phe Met Thr Val Leu Met Tyr Ala
    210                 215                 220

Leu Ser Pro Arg Met Ala Tyr His Phe Ser Glu Cys Val Glu Ser His
225                 230                 235                 240

Ala Tyr Glu Thr Tyr Asp Lys Phe Ile Lys Asp Gln Gly Glu Glu Leu
                245                 250                 255

Lys Asn Leu Pro Ala Pro Lys Ile Ala Val Asp Tyr Tyr Thr Gly Gly
                260                 265                 270

Asp Leu Tyr Leu Phe Asp Glu Phe Gln Thr Ser Arg Glu Pro Asn Thr
    275                 280                 285

Arg Arg Pro Lys Ile Asp Asn Leu Tyr Asp Val Phe Met Asn Ile Arg
    290                 295                 300

Asp Asp Glu Ala Glu His Cys Lys Thr Met Lys Ala Cys Gln Thr His
305                 310                 315                 320

Gly Ser Leu Arg Ser Pro His Thr Asp Pro Cys Asp Ser Glu Asp
                325                 330                 335

Asp Thr Gly Cys Ser Val Pro Gln Ala Asp Cys Ile Gly Ile Val Asp
                340                 345                 350

Cys Ile Lys Lys Ser Val Thr Asp Thr Gln Val Thr Lys Arg
                355                 360                 365

<210> SEQ ID NO 10
<211> LENGTH: 357
<212> TYPE: PRT
<213> ORGANISM: capsicum

<400> SEQUENCE: 10

Met Ala Ile Ser Ile Ser Ala Met Ser Phe Arg Thr Ser Val Ser Ser
1               5                   10                  15

Ser Tyr Ser Ala Phe Leu Cys Asn Ser Lys Asn Pro Phe Cys Leu Asn
                20                  25                  30

Ser Leu Phe Ser Leu Arg Asn Ser His Arg Thr Phe Gln Pro Ser Leu
            35                  40                  45

Ser Arg Lys Ser Arg Val Arg Ala Thr Leu Leu Lys Glu Asn Glu
    50                  55                  60

Glu Glu Val Val Val Glu Lys Ser Phe Ala Pro Lys Ser Phe Pro Gly
65                  70                  75                  80

Asn Val Gly Gly Gly Asn Asn Gly Glu Pro Pro Asp Asn Ser Ser Ser

-continued

```
                   85                  90                  95
Asn Gly Leu Glu Lys Trp Val Ile Lys Ile Glu Gln Ser Val Asn Ile
                100                 105                 110
Phe Leu Thr Asp Ser Val Ile Lys Ile Leu Asp Thr Leu Tyr His Asp
                115                 120                 125
Arg His Tyr Ala Arg Phe Phe Val Leu Glu Thr Ile Ala Arg Val Pro
                130                 135                 140
Tyr Phe Ala Phe Ile Ser Val Leu His Leu Tyr Glu Ser Phe Gly Trp
145                 150                 155                 160
Trp Arg Arg Ala Asp Tyr Leu Lys Val His Phe Ala Glu Ser Trp Asn
                165                 170                 175
Glu Met His His Leu Leu Ile Met Glu Glu Leu Gly Gly Asn Ala Trp
                180                 185                 190
Trp Phe Asp Arg Phe Leu Ala Gln His Ile Ala Val Phe Tyr Tyr Phe
                195                 200                 205
Met Thr Val Ser Met Tyr Ala Leu Ser Pro Arg Met Ala Tyr His Phe
                210                 215                 220
Ser Glu Cys Val Glu His His Ala Tyr Glu Thr Tyr Asp Lys Phe Ile
225                 230                 235                 240
Lys Asp Gln Glu Ala Glu Leu Lys Lys Leu Pro Ala Pro Lys Ile Ala
                245                 250                 255
Val Ser Tyr Tyr Thr Gly Gly Asp Leu Tyr Leu Phe Asp Glu Phe Gln
                260                 265                 270
Thr Ser Arg Glu Pro Asn Thr Arg Arg Pro Lys Ile Asp Asn Leu Tyr
                275                 280                 285
Asp Val Phe Met Asn Ile Arg Asp Asp Glu Ala Glu His Cys Lys Thr
                290                 295                 300
Met Lys Ala Cys Gln Thr His Gly Ser Leu Arg Ser Pro His Thr Asn
305                 310                 315                 320
Pro Cys Asp Glu Ser Glu Asp Pro Gly Cys Ser Val Pro Gln Ala
                325                 330                 335
Asp Cys Val Gly Ile Val Asp Cys Ile Thr Lys Ser Val Ala Asp Pro
                340                 345                 350
Asn Val Gly Arg Arg
                355
```